United States Patent [19]
Goble et al.

[11] Patent Number: 5,647,869
[45] Date of Patent: Jul. 15, 1997

[54] ELECTROSURGICAL APPARATUS

[75] Inventors: Nigel Mark Goble, Castleton; Colin Charles Owen Goble, South Glamorgan, both of Wales

[73] Assignee: Gyrus Medical Limited, St. Mellons, United Kingdom

[21] Appl. No.: 496,208

[22] Filed: Jun. 28, 1995

[30] Foreign Application Priority Data

Jun. 29, 1994 [GB] United Kingdom .................. 9413070

[51] Int. Cl.$^6$ ........................................... A61B 17/39
[52] U.S. Cl. .................. 606/37; 606/39; 606/40; 606/45; 606/48; 606/49; 606/50
[58] Field of Search .............................. 606/37–42, 45, 606/48–51

[56] References Cited

U.S. PATENT DOCUMENTS 3,707,149 12/1972 Hao et al. .......................... 606/45
3,870,047 3/1975 Gonser ............................. 606/45
3,875,945 4/1975 Friedman ......................... 606/45

FOREIGN PATENT DOCUMENTS 1215305 4/1960 France ............................ 606/40
932705 7/1963 United Kingdom .............. 606/42

*Primary Examiner*—Lee S. Cohen
*Attorney, Agent, or Firm*—Peter C. Richardson; Lawrence C. Akers; Aaron Passman

[57] ABSTRACT

In electrosurgical apparatus for tissue desiccation and cutting, an electrosurgical generator has a series-connected output inductor which forms a series resonant circuit with the capacitance of the generator load, the load including an electrode unit and a cable coupled to the generator output. The series resonant frequency is typically 1.5 f where f is the operating frequency of the generator. A capacitor may be included, coupled between the conductors which connect bipolar electrodes to the generator, to increase the load capacitance. The effect of these measures is to boost the output voltage available for electrosurgical treatment, especially for tissue cutting.

14 Claims, 1 Drawing Sheet

ELECTROSURGICAL APPARATUS

FIELD OF THE INVENTION

This invention relates to electrosurgical apparatus including circuitry for increasing the radio frequency power applied during surgery and especially during electrosurgical cutting.

BACKGROUND OF THE INVENTION

Electrosurgical cutting generally requires a higher output voltage than electrosurgical desiccation. To provide for this, it is known to include within an electrosurgical generator an output transformer which has a higher secondary-to-primary output transformer turns ratio for cutting compared with that used for desiccation. Such increased turns ratio leads to increased demands on the output device driving the transformer, particularly in terms of the peak output current required and power dissipation. To overcome this difficulty, it is known to increase the output impedance of the generator, typically to a value in the range of from 300Ω to 500Ω. This may be achieved by providing a low value coupling capacitor but this has the disadvantage of increased voltage drop across the coupling capacitor when used in high load impedance conditions due to the inherent capacitance of the electrode assembly and any cable coupling the electrode assembly to the generator. In effect, the inherent capacitance represents a capacitive load impedance which produces, with the coupling capacitor, a potential divider reducing the voltage delivered across the load. The problem becomes worse when the electrode assembly is placed in a wet field (e.g. in blood or saline solution), since then the effective load capacitance is increased.

It is an object of this invention to overcome this disadvantage.

SUMMARY OF THE INVENTION

According to this invention, there is provided electrosurgical apparatus comprising an electrosurgical generator coupled to an electrical load which includes an electrosurgical electrode unit and at least one conductor coupling the electrode unit to the generator, wherein the generator has an in-line output inductor in series with the coupling conductor, and wherein the load is capacitive, the capacitance of the load and the output inductor together forming a series resonant output circuit having a resonant frequency which is higher than the operating frequency of the generator yet is not higher than twice the said operating frequency. Although the load capacitance may be composed entirely of the inherent capacitance between the conductor and the electrode unit and neighbouring conductive elements, it is preferred that it also includes at least one capacitor, i.e. a lumped capacitance, additional to the inherent capacitance, coupled across the output of the generator. As an addition or alternative to the lumped capacitance, a high capacitance cable may be used containing conductors coupling the generator to the electrode unit.

In one embodiment of the invention, the electrode unit is housed, detachably or non-detachably, in a handpiece which is coupled to output terminals of the generator by a cable. Coupling conductors from the generator output extend through the cable and the handpiece to electrodes on the electrode unit. In this embodiment, the handpiece contains a capacitor coupled across the conductors, thereby to be coupled across the output terminals of the generator when the handpiece is connected. Since handpieces can be supplied with cables of different lengths, the value of the capacitor in any particular handpiece may be chosen at least in part to suit the length of the cable with which it is supplied. Thus, because the inherent capacitance of the conductors in the cable is dependent on the cable length, the capacitor can be selected to yield a required overall or total capacitance value for the combination of the handpiece and cable. Having the capacitor in the handpiece also yields the advantage that, if required, a switch can be provided in the handpiece in series with the capacitor for connecting and disconnecting the capacitor according to the output characteristics required. Indeed, it is possible to include more than one capacitor so that alternative capacitor values can be selected by the user.

By providing an in-line inductor together with a capacitance across the generator output terminals, and provided that the Q of the resulting series resonant circuit at the operating frequency of the generator is greater than 1, the voltage available across the load, in effect across the capacitance, is higher than achieved in the prior art, even without increasing the number of turns on the secondary winding of the output transformer of a transformer coupled generator output stage. As has already been stated, the resonant frequency of the series resonant combination is preferably higher than the operating frequency of the generator. The preferred range for a given load impedance is 1.25 f to 2 f where f is the generator frequency at that which maximum power transfer to the load occurs in open loop conditions (i.e. without feedback-controlled modulation which causes output power variation in response to load impedance variation). At the generator frequency, the Q of the series resonant combination may be in the range of from 1.5 to 3.

With the resonant frequency higher than the generator operating frequency, the series resonant combination is permanently out of tune. This deliberate mismatch has two advantages. Firstly, when the electrode unit is used in a wet field, the increased capacitance results in a lower resonant frequency for the series resonant combination, bringing the resonant frequency closer to the operating frequency of the generator and consequently increasing the voltage delivered to the load. In this way, the effect of conductive fluid in the region of the electrodes is compensated for by an increase in output voltage beyond that which would otherwise be achieved. Furthermore, the tuning of the series resonant combination is not especially critical since it is used outside its resonant peak impedance, i.e. at points on its impedance versus frequency characteristic where the slope of the characteristic is less steep than nearer the resonant frequency.

The operating frequency of the generator may be variable according to load impedance at its output. Typically, the operating frequency remains within the range of from 300 kHz to 500 kHz. The resonant frequency of the series resonant circuit is typically between 450 kHz and 700 kHz with the preferred frequency in dry conditions being in the range 500 kHz to 600 kHz. Typical values for the in-line inductor are 150 µH to 250 µH, with the preferred range being 170 µH to 210 µH. The total capacitance of the electrode unit, and elements between the electrode unit and the output terminals of the generator, may be arranged so as to be greater than 350 pF and preferably greater than 400 pF.

In the case of the electrosurgical generator having a single output for both cutting and desiccation, it is preferable for the in-line inductor to be switched, so that it forms part of the power delivery path through the output stage of the generator when cutting is required, and is switched out or bypassed when a lower voltage output is required, as in desiccation. It is possible to combine the generator within a handpiece which mounts the electrode unit, in which case a simple switch may be provided on the handpiece casing. In the more common situation of the generator being a separate unit connected to a handpiece via a cable, the switch may be provided on the generator housing itself or, preferably, the switching of the inductor may be performed by remote control from a switch on the handpiece. Indeed, the switch may be operated using the same control as a second switch for switching the generator on and off. This may be achieved by including one or more further conductors in the cable between the handpiece and the generator, the handpiece containing two switch elements, each operating a relay in the generator via a transformer-coupled link, for instance. It is possible to operate both switch elements in the handpiece from a single control button so that the surgeon can apply electrosurgical power with a first depression of the button and then, if required, can increase the output voltage for cutting by switching in the in-line inductor with a further depression of the button beyond the depression required for switching the generator on.

The invention includes, in accordance with a second aspect thereof, an electrosurgical instrument comprising: a bipolar electrode unit; and a handpiece mounting the electrode unit; the handpiece including a pair of power supply conductors for delivering electrosurgical radio frequency power from a generator to the electrodes of the electrode unit, and a capacitor connected across the conductors to supplement the inherent capacitance of the electrode unit and the power supply conductors.

DESCRIPTION OF PREFERRED
EMBODIMENTS OF THE INVENTION

Figure 1:
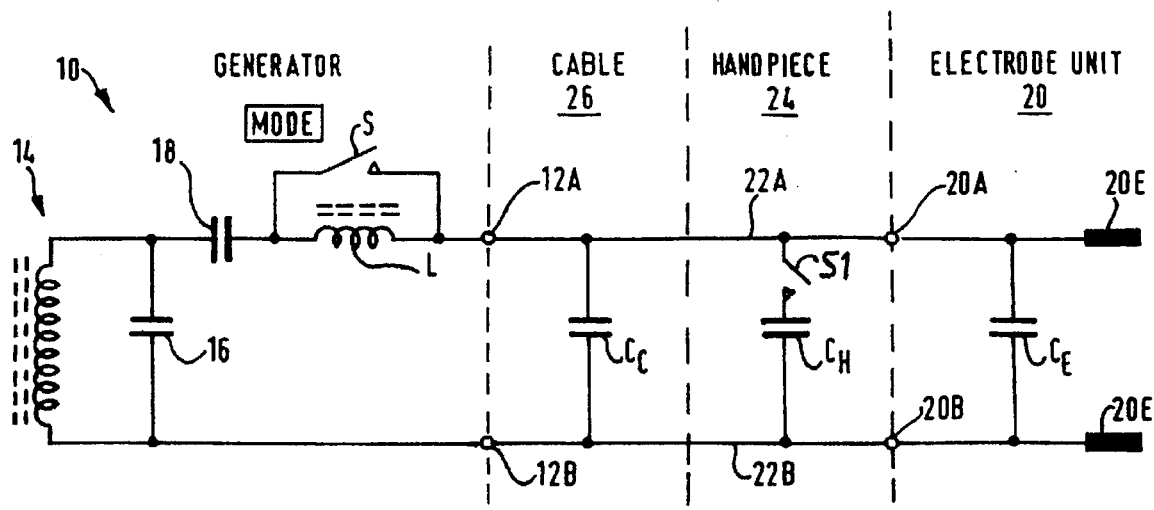
FIG. 1 is a simplified circuit diagram of electrosurgical apparatus in accordance with the invention.

A preferred embodiment of the invention is shown in simplified form in FIG. 1. Electrosurgical apparatus has a radio frequency electrosurgical generator with an output stage 10 having output terminals 12A, 12B. The generator is preferably of the form disclosed in British Patent No. 2214430, at least insofar as it has a self-tuning output oscillator having a resonant output circuit comprising the secondary winding 14 of an output transformer, a first capacitor 16 coupled in parallel across the secondary winding and a second capacitor 18 coupled in series between the transformer secondary winding and one of the output terminals 12A, 12B of the generator. Accordingly, the resonant frequency of the resonant output circuit is determined in part by the impedance of the load presented to the generator across its terminals 12A, 12B due to the series-connected reactance element represented by the second capacitor 18. The generator has means (not shown) for pulsing the oscillator to regulate the output power. This is achieved by means of a feedback loop. References to open loop conditions in this specification means operation of the generator with that feedback loop disabled.

The apparatus further includes a bipolar electrode unit 20 having electrodes 20E, the unit being coupled to the generator by power delivery conductors 22A, 22B, each conductor electrically linking a respective electrode to a respective one of the output terminals 12A, 12B of the generator. The conductors 22A, 22B pass from the electrodes 20E through a handpiece 24 which mounts the electrode unit 20, and through a cable 26 joining the handpiece to the generator. It will be noted that in this preferred embodiment, the electrode unit has terminals 20A and 20B allowing detachable electrical connection between the electrode unit 20 and the handpiece 24, and that the handpiece 24 is permanently connected to the cable 26 which, in turn, is detachable from the terminals 12A, 12B of the generator 10. This means that the handpiece and the cable form an assembly which is preferably supplied as a unit.

In accordance with the invention, the generator includes an in-line inductor L forming a series element in one of the power delivery paths between the secondary winding 14 of the output stage transformer and one of the conductors 22A, 22B. It will be appreciated that the conductors 22A, 22B have an inherent parallel capacitance, particularly in the cable 26 where they are located close together. This capacitance is shown in FIG. 1 as capacitance $C_C$. Similarly, the electrode unit has an inherent parallel capacitance $C_E$, which is also shown diagrammatically as a lumped component in FIG. 1. Capacitance $C_E$ varies according to the conditions at the electrodes 20E. In a wet field, $C_E$ will be considerably higher than when the unit is dry, due to conductive fluids being in contact with the exposed conductive surfaces of the electrodes 20E. To these inherent capacitances $C_C$ and $C_E$, there is added a capacitor $C_H$ in the handpiece 24, this capacitance being a capacitor component of predetermined value. The total load capacitance $C_C+C_H+C_E$ forms a series resonant circuit with the in-line inductor L. A first switch, shown as S1 in FIG. 1, is used to electrically connect the capacitance CH.

The generator operating frequency varies between about 340 kHz and 440 kHz without the inductor L in the output circuit. A typical value for inductor L is 175 µH. The value of capacitor $C_H$ is chosen so that the resonant frequency of the series resonant circuit is about 1.5 $f_{gen}$, where $f_{gen}$ is the operating frequency of the generator at which maximum power transfer to the load occurs in open loop conditions with inductor L switched out. (This corresponds in the present case to a load resistance of about 100Ω.) Typically, this gives a value of between 400 pF and 500 pF for the total load capacitance $C_C+C_H+C_E$ in dry conditions. In practice, the electrode unit in dry conditions has a capacitance of about 20 pF with the remainder of the capacitance being split between the handpiece and the cable. $C_H$ is typically in the range of from 150 pF to 350 pF.

Capacitor 18 is about an order of magnitude greater than the total load capacitance $C_C+C_H+C_E$. Consequently, the series resonant circuit formed by inductor L and the load capacitance has a relatively minor effect on the operating frequency of the generator 10.

It will be appreciated that in an embodiment in which the generator is integrated in the handpiece, the inherent capacitance of the conductors 22A, 22B will be considerably less than in the illustrated embodiment. In such a case, the capacitor $C_H$ will be correspondingly large.

A by-pass switch S is connected across the inductor L to allow it to be switched in or out as required depending on the nature of the electrosurgery being performed.

The added capacitance which is represented by $C_H$ in the embodiment of FIG. 1 need not necessarily be incorporated in the handpiece. In particular it could be incorporated by choosing a cable of suitable length and with a high inherent capacitance, e.g. greater than 100 pF or greater even than 200 pF per meter.

Figure 2:
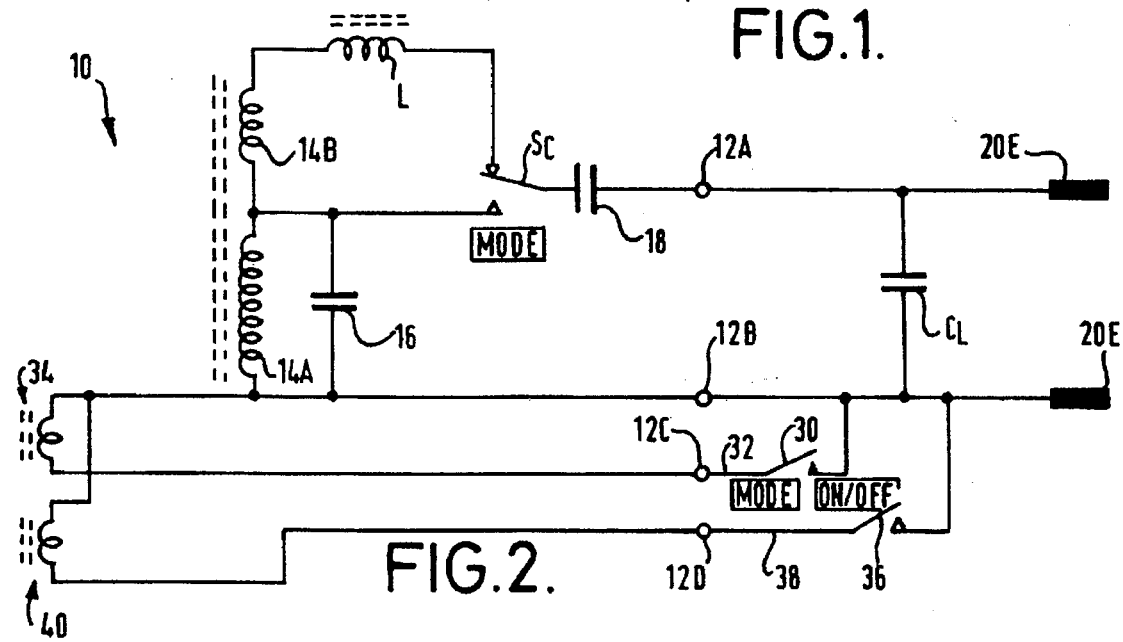
FIG. 2 is a circuit diagram of part of alternative apparatus in accordance with the invention.

While the arrangement shown in FIG. 1 results in an increased output voltage across the electrodes 20E when the load impedance is comparatively high (e.g. 1 kΩ upwards), a further improvement can be achieved by increasing the number of turns on the secondary winding of the generator transformer as illustrated in FIG. 2. Here, the secondary winding is in two portions 14A, 14B, the capacitor 16 being coupled across the larger main portion 14A of the secondary winding only. In this embodiment, portion 14A has twice the number of turns as portion 14B. In-line inductor L is coupled in series between the generator output stage (specifically the secondary winding portion 14B) and one of the output terminals 12A, 12B. In this case, the second capacitor 18 of the resonant circuit, which influences the frequency of the self-tuning oscillator of the generator, is connected between in-line inductor L and output terminal 12A. It will be appreciated that when the in-line inductor is in circuit, the order of connection of the capacitor 18 and inductor L is immaterial. The cable, handpiece, and electrode unit are shown in simplified form with a single load capacitance $C_L$ constituted by the capacitors $C_C$, $C_H$, and $C_E$ of FIG. 1.

In this embodiment, the in-line inductor L is switched in and out of the input circuit together with the additional secondary winding 14B by a changeover switch element $S_C$ so that for desiccation, the output terminals 12A, 12B are connected across the main part 14A of the secondary winding only. When a higher output voltage is required, e.g. for electrosurgical cutting, switch element $S_C$ is operated to connect the generator output terminals instead across both secondary winding portions 14A, 14B in combination with the series or in-line inductor L. As before, a series resonant circuit is formed by in-line inductor L and load capacitance $C_L$, the resonant frequency being higher than the generator operating frequency over the majority, if not all, of the operating frequency range.

Switch element $S_C$ is preferably the armature and contacts of a changeover relay. For convenience, this relay can be operated remotely by a push button switch (not shown) on the handpiece which, when activated, closes a switch 30 which is connected through a wire 32 in the cable and a connector 12C, to an operating coil 34 in the generator 10. The same push button may be used to operate another switch 36 in the handpiece connected by another wire 38 and another connector 12D to another coil 40 in the generator for switching the generator output on or off.

Figure 3:
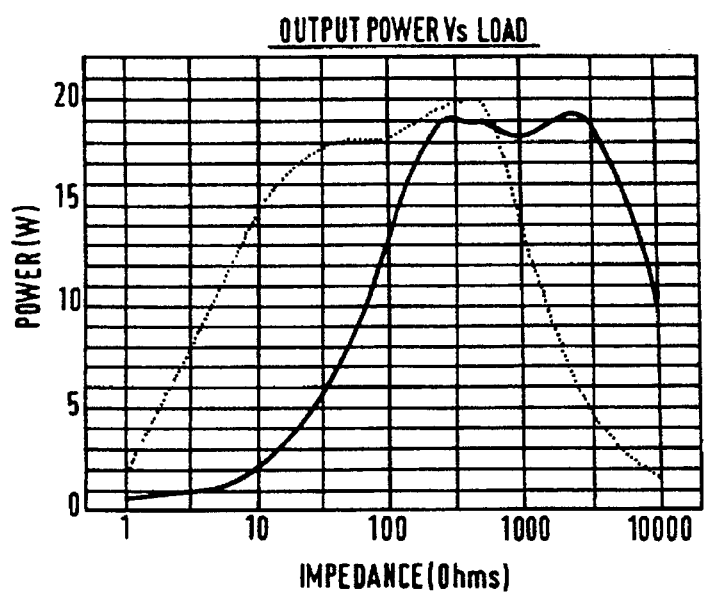
FIG. 3 a graph showing the variation of output power with load impedance.

The effect of switching in the in-line inductor L in the circuit of FIG. 2 is shown in FIG. 3, which is a graph plotting the output power delivered to the load as a function of load impedance, the generator output being pulse width modulated to limit the power, in this case, to about 20 watts. The dotted curve shows the power/impedance characteristic with in-line inductor L switched out. This setting would be used for desiccation. The solid line curve shows the effect of switching in the in-line inductor L. It will be noted that the power output at higher load impedances is substantially increased and, additionally, on a logarithmic scale, the width of the power curve is increased. Both curves have an approximately flat central portion. In these portions, the output power is limited by pulsing the oscillator.

What is claimed is:

1. Electrosurgical apparatus comprising:
   an electrosurgical generator having a generator output coupled to an electrical load which includes an electrosurgical electrode unit, and
   at least one coupling conductor which connects the electrode unit to the generator output,
   wherein the generator has a resonant output network determining an operating frequency, and
   wherein the resonant output network has an in-line output inductor connected in series with the coupling conductor, and
   wherein the load is capacitive, the capacitance of the load and the output inductor together forming a series resonant output circuit having a resonant frequency which is higher than the operating frequency of the generator yet is not higher than twice the said operating frequency.

2. Apparatus according to claim 1, wherein the electrical load includes at least one capacitor forming a lumped capacitance coupled across the generator output.

3. Apparatus according to claim 2, wherein the electrode unit is housed in a handpiece and the capacitor is located in the handpiece.

4. Apparatus according to claim 3, wherein the electrode unit is a bipolar unit having a pair of electrodes each of which is connected to a respective output terminal of the generator by a respective conductor passing through the handpiece, and wherein the capacitor is connected between the conductors.

5. Apparatus according to claim 3, including a first switch for connecting and disconnecting the capacitor.

6. Apparatus according to claim 5, wherein the first switch is in the handpiece.

7. Apparatus according to claim 1, wherein the said resonant frequency is equal to Kf, K being in the range of from 1.25 to 2 and f being the generator frequency at which maximum power transfer to the load occurs in open loop conditions.

8. Apparatus according to claim 1, wherein Q of the series resonant circuit is in the range of from 1.5 to 3.

9. Apparatus according to claim 1, wherein the operating frequency of the generator is in the range of from 300 kHz to 500 kHz and the inductor has a value in the range of from 150 µH to 250 µH.

10. Apparatus according to claim 1, wherein the generator has a single output for cutting and desiccation and a switch which is connected such that the inductor forms part of a power delivery path to the load when the switch is in a cutting mode state, and the inductor is bypassed when the switch is in a desiccation mode state.

11. An electrosurgical generator having a power supply and a waveform shaping network for generating high frequency electrical power for surgical operations, the electrosurgical generator further comprising:
   an output stage having a parallel resonant output circuit forming part of a resonant output network determining an operating frequency of the generator,
   an output terminal for connection to an electrode unit by means of a coupling conductor, and, connected in series between the resonant output circuit and the terminal, an inductor for forming a series resonant circuit with a capacitive load when connected to the terminal, the series resonant circuit tuned to a frequency higher than the operating frequency yet not higher than twice the operating frequency.

12. A generator according to claim 11, wherein the generator is operable at a frequency in the range of from 300 kHz to 500 kHz and the value of the inductor is in the range of from 150 µH to 250 µH.

13. A generator according to claim 11, wherein the generator includes a mode control for switching between desiccation and cutting modes, the mode control including a switch which is so connected that in the desiccation mode the inductor is bypassed, and in the cutting mode the inductor is connected in series between the resonant output circuit and the terminal.

14. An electrosurgical instrument comprising a bipolar electrode unit having inherent capacitance; and a handpiece mounting the electrode unit; the handpiece including a pair of power supply conductors for delivering electrosurgical radio frequency power from a generator to the electrodes of the electrode unit, and a capacitor connected across the conductors to supplement the inherent capacitance of the electrode unit and the power supply conductors.

* * * * *